(12) United States Patent
Ran et al.

(10) Patent No.: US 11,543,406 B2
(45) Date of Patent: Jan. 3, 2023

(54) CHEMILUMINESCENCE IMMUNOASSAY ANALYZER

(71) Applicant: CHENGDU SEAMATY TECHNOLOGY CO., LTD., Sichuan (CN)

(72) Inventors: Peng Ran, Sichuan (CN); Xianghong Zeng, Sichuan (CN); Peng Wang, Sichuan (CN); Biao Mu, Sichuan (CN); Zihua Han, Sichuan (CN); Luwei Ye, Sichuan (CN)

(73) Assignee: CHENGDU SEAMATY TECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 17/427,105

(22) PCT Filed: Jul. 22, 2020

(86) PCT No.: PCT/CN2020/103486
§ 371 (c)(1),
(2) Date: Jul. 30, 2021

(87) PCT Pub. No.: WO2021/217909
PCT Pub. Date: Nov. 4, 2021

(65) Prior Publication Data
US 2022/0252579 A1 Aug. 11, 2022

(30) Foreign Application Priority Data

Apr. 26, 2020 (CN) .......................... 202010339131.8

(51) Int. Cl.
*G01N 21/13* (2006.01)
*G01N 21/76* (2006.01)
(Continued)

(52) U.S. Cl.
CPC ......... *G01N 33/5302* (2013.01); *G01N 21/13* (2013.01); *G01N 21/15* (2013.01);
(Continued)

(58) Field of Classification Search
None
See application file for complete search history.

(56) References Cited

U.S. PATENT DOCUMENTS 4,349,510 A * 9/1982 Kolehmainen .. G01N 35/00009
435/808
4,960,566 A 10/1990 Mochida
(Continued)

FOREIGN PATENT DOCUMENTS

| CN | 109490559 | 3/2019 |
|----|-----------|--------|
| CN | 110261632 | 9/2019 |

(Continued)

OTHER PUBLICATIONS

"International Search Report (Form PCT/ISA/210) of PCT/CN2020/103486," dated Jan. 27, 2021, pp. 1-4.
(Continued)

*Primary Examiner* — Neil N Turk
(74) *Attorney, Agent, or Firm* — JCIP Global Inc.

(57) ABSTRACT

The present invention discloses a chemiluminescence immunoassay analyzer, including a rotating disc assembly for carrying and thermal insulation of capillary tubes, an air-blowing assembly for removing residual liquid from the capillary tubes, a detection assembly for detecting the number of luminescent photons in the capillary tubes, and a bottom plate for installing the rotating disc assembly, the air-blowing assembly, and the detection assembly. The present invention further includes a charging and recycling system and a sample feeding assembly, wherein the charging and recycling system includes a fixed seat, a capillary tube
(Continued)

push-out device, a storage device, a first driving device, and a waste liquid recycling device; the capillary tube push-out device is used for pushing capillary tubes out of the storage device and squeezing out reagents stored in the storage device; the storage device is used for storing the reagents and providing the coated capillary tubes.

10 Claims, 19 Drawing Sheets

(51) Int. Cl.
    *G01N 33/53* (2006.01)
    *G01N 35/02* (2006.01)
    *G01N 35/00* (2006.01)
    *G01N 35/10* (2006.01)
    *G01N 35/04* (2006.01)
    *G01N 21/15* (2006.01)
    *G01N 21/01* (2006.01)

(52) U.S. Cl.
    CPC ..... *G01N 21/76* (2013.01); *G01N 2021/0112* (2013.01); *G01N 2021/151* (2013.01)

(56) References Cited

U.S. PATENT DOCUMENTS 5,976,896 A * 11/1999 Kumar ................. G01N 35/00
    422/417
2006/0141494 A1* 6/2006 Kambara ........... G01N 21/6428
    435/6.13

FOREIGN PATENT DOCUMENTS

| | | |
|---|---|---|
| CN | 110514859 | 11/2019 |
| CN | 111337480 | 6/2020 |
| CN | 111337481 | 6/2020 |
| CN | 212059920 | 12/2020 |
| CN | 212059921 | 12/2020 |
| CN | 110514859 | 3/2021 |
| EP | 1912071 | 4/2008 |
| WO | WO-2019016546 A1 * 1/2019 ............ B01L 3/5085 |

OTHER PUBLICATIONS

"Written Opinion of the International Searching Authority (Form PCT/ISA/237) of PCT/CN2020/103486," dated Jan. 27, 2021, pp. 1-5.

* cited by examiner

CHEMILUMINESCENCE IMMUNOASSAY ANALYZER

CROSS-REFERENCE TO RELATED APPLICATION

This application is a 371 of international application of PCT application serial no. PCT/CN2020/103486, filed on Jul. 22, 2020, which claims the priority benefit of China application no. 202010339131.8, filed on Apr. 26, 2020. The entirety of each of the above mentioned patent applications is hereby incorporated by reference herein and made a part of this specification.

TECHNICAL FIELD

The present invention relates to a chemiluminescence immunoassay analyzer, which is an analyzer for immunoassay using chemiluminescence and belongs to the technical field of chemiluminescence assays.

BACKGROUND

The ChemiLuminescence (CL) method is a type of molecular luminescence spectrum analysis methods. It is mainly a trace analysis method of using analyzers to detect the chemiluminescence intensity of a system and determining the content of an analyte according to a principle that the concentration of an analyte in a chemical detection system and the chemiluminescence intensity of the system are in linear quantitative relationships under certain conditions. The chemiluminescence method is widely used in the analysis of trace metal ions and various types of inorganic and organic compounds as well as in biological fields.

Chemiluminescence immunoassay (CLIA) is a technique of combining highly-sensitive chemiluminescence assays with highly-specific immune responses to detect and analyze various types of antigens, antibodies, hormones, enzymes, vitamins, drugs, and the like. It is an immunoassay technique developed after radioimmunoassay, enzyme immunoassay, fluoroimmunoassay, and time-resolved fluoroimmunoassay. The chemiluminescence method has advantages such as high sensitivity, high specificity, high accuracy, and wide detection range. Compared with the semi-quantitative enzyme-linked immunosorbent assay (ELISA) method, the chemiluminescence method is truly quantitative, and it detects faster and is more convenient to use. Meanwhile, the chemiluminescence markers are stable and the reagents have a long effective period, which greatly facilitates clinical applications.

An invention patent with the application number of CN201910774133.7 and the publication number of CN110514859A discloses a full-automatic chemiluminescence immunoassay method. According to the method, a capillary tube storage assembly, a capillary tube push-out assembly, a rotating disc assembly, an air-blowing assembly, a sample assembly, a reagent assembly, and a detection assembly need to be installed first. Then, the capillary tube push-out assembly is started to push capillary tubes out of the capillary tube storage assembly and into the rotating disc assembly. The rotating disc assembly rotates to convey the capillary tubes to the sample assembly, the air-blowing assembly, the reagent assembly, and the detection assembly. Therefore, automatic immunoassay is achieved. This invention uses capillary tubes as carriers instead of ELISA plates or microwell plates in the prior art, which greatly reduces the quantities of samples and reagents required, lowers the detection cost, and improves the detection efficiency.

The specification of the above invention also discloses an immunoassay device for implementing the assay method. However, the following defects still exist in the actual implementation.

1. Plenty of spaces inside the immunoassay analyzer are underutilized, the working positions are scattered, and the number of the working positions is large, so that the analyzer is oversized;
2. When blood samples are to be fed, a small number of samples will be fed, and they cannot be tested upon arrival and shall wait for testing;
3. When the capillary tubes are to be pushed out, the capillary tube push-out mechanism may collide with the capillary tube storage assembly during positioning, which may affect the position accuracy of each part after multiple times of use and cause malfunctions in the analyzer;
4. The capillary tube storage assembly is kept in communication with the interior of the analyzer, and dust may enter the capillary tube storage assembly from outside the analyzer, so that the cleanliness of the capillary tubes will be affected and errors will occur in the detection results.

SUMMARY

The objective of the present invention is to provide a chemiluminescence immunoassay analyzer. The present invention achieves precise fitting and more compact installation at each working position. The analyzer is smaller in size and occupies less space, and is thus more miniaturized. Besides, it can effectively improve the detection efficiency.

To solve the above technical problem, the present invention adopts the following technical solution.

The present invention discloses a chemiluminescence immunoassay analyzer with the following structure.

The chemiluminescence immunoassay analyzer includes a rotating disc assembly for carrying and thermal insulation of capillary tubes, an air-blowing assembly for removing residual liquid from the capillary tubes, a detection assembly for detecting the number of luminescent photons in the capillary tubes, and a bottom plate for installing the rotating disc assembly, the air-blowing assembly, and the detection assembly; characterized in that the analyzer further includes a charging and recycling system and a sample feeding assembly, wherein the charging and recycling system includes a fixed seat, a capillary tube push-out device, a storage device, a first driving device, and a waste liquid recycling device.

The capillary tube push-out device is used for pushing capillary tubes out of the storage device and squeezing out reagents stored in the storage device.

The storage device is used for storing the reagents and providing the coated capillary tubes.

The sample feeding assembly is used for providing samples.

The waste liquid recycling device is used for recycling the reagents overflowing and dripping from the storage device.

The fixed seat and the waste liquid recycling device are fixedly installed on the bottom plate, the capillary tube push-out device is slidably installed on the fixed seat through a first guide rail and a first guide block, the first driving device is connected to the capillary tube push-out device and is configured for driving the capillary tube push-out device to move on the fixed seat, and the storage device is slidably installed on the capillary tube push-out device and is configured for moving on the capillary tube push-out device.

The waste liquid recycling device is located at a central position of the bottom plate, the rotating disc assembly is located on a left side of the waste liquid recycling device, and the air-blowing assembly, the detection assembly, the capillary tube push-out device, the storage device, and the sample feeding assembly are located on a right side of the waste liquid recycling device.

Each part of the present invention is further described below.

The specific structure of the sample feeding assembly is as follows. The sample feeding assembly includes a bracket, and rotating shafts are rotatably installed on left and right ends of the bracket, respectively; two pulleys are rotatably installed on the rotating shafts, respectively, and the two pulleys are connected through a belt; a drive motor is fixedly installed on a side surface of the bracket, and an output shaft of the drive motor is connected to one of the rotating shafts; a groove is provided on an inner side surface of the belt, and a depression is disposed on each of the two pulleys and at a position corresponding to the groove on the belt; several bearing holes are arranged at equal intervals in the belt along a length direction thereof, the bearing holes are in communication with the groove, and a sample bearing cup is arranged in each of the bearing holes; a positioning column with gaps is disposed on a bottom of the sample bearing cup, and the sample bearing cup is connected to the bearing hole in the belt through the positioning column by means of interference fit.

A bracket slidable assembly below the bracket is connected to a bracket driving assembly, and the bracket driving assembly is configured for driving the bracket to move.

The bracket slidable assembly includes a bracket slider and a bracket slide rail, the bracket slider is installed on a bottom of the bracket, the bracket slide rail is installed on the bottom plate of the chemiluminescence immunoassay analyzer, and the bracket slider cooperates with the bracket slide rail.

Preferably, limiting protrusions are disposed on two sides of the bottom of the bracket, an area for installing the bracket slider is formed between the limiting protrusions, and the bracket slider is installed in this area.

It should be noted that, the bracket driving assembly is a pneumatic driving assembly, a hydraulic driving assembly, a leadscrew driving assembly, or a gear-rack driving assembly.

The gear-rack driving assembly is further described below. The gear-rack driving assembly includes a bracket gear, a bracket rack, and a bracket motor. The bracket motor is installed on the bottom plate of the chemiluminescence immunoassay analyzer, the bracket rack is installed on a side surface of the bracket, the bracket gear is fixedly installed on an output shaft of the bracket motor, and the bracket gear meshes with the bracket rack.

Preferably, the pulley is a toothed pulley, the belt is a toothed belt, and the depression is disposed in the middle of the teeth of the toothed pulley.

Preferably, a bracket sensor is installed on the bracket and is close to one of the pulleys, detection gaps are disposed on the edge of the pulley, and the bracket sensor is connected to the drive motor.

The specific structure of the storage device is as follows. The storage device includes a storage seat, a translation mechanism, and several storage assemblies; the translation mechanism is used for driving the storage seat to move; the storage assemblies are arranged side by side on the storage seat and each mainly consist of a reagent storage box and a capillary tube storage box connected above the reagent storage box; the reagent storage box is used for storing reagents, and the capillary tube storage box is used for storing coated capillary tubes; an L-shaped installation portion is connected on a side surface of the reagent storage box, a hook is disposed on the L-shaped installation portion, a slot is provided on a side surface of the storage seat, and the hook is configured for being engaged with the slot; two positioning protrusions are disposed on a bottom surface of the reagent storage box and are each provided with a limiting slot; a bolt clamping area is formed between the two limiting slots; a transverse groove is disposed on the storage seat and divides the storage seat into a left part and a right part, and the left part is lower than the right part; several separating grooves are disposed in the right part, and the separating grooves are in communication with the transverse groove and divide the right part into several bumps; each of the separating grooves between the bumps forms a positioning protrusion installation area, a through-hole is provided on a side surface of each of the bumps, and after the hook of the L-shaped installation portion is engaged with the slot, the two positioning protrusions are located in the positioning protrusion installation area and are limited by a bolt passing through the through-holes in the bumps; therefore, the storage assembly is fixed on the storage seat.

A reagent chamber is formed inside the reagent storage box, a reagent tube is disposed on a side wall of the reagent storage box, the reagent tube is in communication with the reagent chamber, and a rubber film is disposed on a side wall of the reagent storage box opposite to the reagent tube; when the rubber film is pressed, the reagents in the reagent chamber flow out of the reagent tube and a reagent droplet is formed at an outlet of the reagent tube.

A capillary tube storage chamber is formed through partition plates in the capillary tube storage box; the capillary tube storage chamber is wider than a diameter of the capillary tube by 0.5-1 mm, and several capillary tubes are vertically stacked in order inside the capillary tube storage chamber; a left-side through-hole and a right-side through-hole are respectively disposed on a left side and a right side at a bottom of the capillary tube storage box; the left-side through-hole and the right-side through-hole are both in communication with the capillary tube storage chamber; rubber film flaps capable of being opened or closed are disposed at the left-side through-hole and the right-side through-hole.

Preferably, the center of the rubber film flap has cross-shaped, Y-shaped, and X-shaped scratches, so that the rubber film flap can be closed after the capillary tube gets in or out.

A cleaning liquid tank is installed on the storage seat.

It should be noted that, the translation mechanism is a pneumatic translation mechanism, a hydraulic translation mechanism, a gear-rack translation mechanism, a leadscrew translation mechanism, or an electric push-rod translation mechanism.

The translation mechanism is connected to a detection sensor, and the detection sensor is used for detecting the positions of the storage assemblies.

Preferably, a buffering pad is disposed on side surfaces of the capillary tube storage box and the reagent storage box, a circular hole is provided in the buffering pad, and the position of the circular hole is corresponding to those of the left-side through-hole and the rubber film flap.

The specific structure of the capillary tube push-out device is as follows. The capillary tube push-out device includes a positioning bracket, a positioning assembly, and a pushing assembly; the positioning bracket is slidably installed on the fixed seat, the positioning assembly and the pushing assembly are slidably installed on the positioning bracket, and the positioning assembly is located in front of the pushing assembly; the positioning assembly and the pushing assembly are each connected to a push-out driving device, and the push-out driving devices are configured for driving the positioning assembly and the pushing assembly to move on the positioning bracket, respectively; the positioning assembly is connected to a press rod; the press rod is used for pressing the rubber film on the reagent storage box of the storage device in the chemiluminescence immunoassay analyzer; the positioning assembly is used for positioning the left-side through-hole in the capillary tube storage box of the storage device in the chemiluminescence immunoassay analyzer; the pushing assembly is used for pushing the capillary tube out of the right-side through-hole in the capillary tube storage box of the storage device in the chemiluminescence immunoassay analyzer.

Specifically, the positioning assembly includes a positioning rack, a positioning rod, a blocking plate, and a spring; the positioning rack is connected to one of the push-out driving devices, and the push-out driving device is used for driving the positioning rack to move; the positioning rod is hollow inside, one end of the positioning rod is tapered and the other end thereof is provided with a first limiting boss, and the tapered end of the positioning rod is provided with a second limiting boss; the positioning rod is slidably installed on the positioning rack and has the two ends extending out of the positioning rack; the spring and the blocking plate are both sleeved on the positioning rod, the blocking plate is close to the first limiting boss, and the spring is close to the second limiting boss; under the action of the spring, the first limiting boss presses the blocking plate on a side surface of the positioning rack; a push rod in the pushing assembly is configured for passing through the positioning rod to push the capillary tube; the press rod is installed on the positioning rack, and the press rod is shorter than the positioning rod extending from the right end of the positioning rack.

As a further limitation, the pushing assembly includes a push rack and the push rod; the push rack is connected to the other push-out driving device, and the push-out driving device is configured for driving the push rack to move; one end of the push rod is connected to the push rack and the other end thereof extends into the positioning rod and then out of the positioning rod.

The pushing assembly further includes an adjustment bolt, a threaded hole and a guide hole are provided in the push rack, the threaded hole is in communication with the guide hole, and the adjustment bolt matches with the threaded hole; the push rod is connected to the push rack through the adjustment bolt; one end of the push rod passes through the guide hole and is fixedly connected to an end of the adjustment bolt and the other end thereof extends into the positioning rod; after the positioning rack moves, the push rod extends out of the positioning rod.

Further, the positioning assembly and the pushing assembly are connected to the two push-out driving devices through a sliding assembly separately. The sliding assembly includes a sliding guide rail, a positioning slider, and a push-out slider. The sliding guide rail is fixedly installed on the positioning bracket, the positioning slider and the push-out slider are slidably arranged on the sliding guide rail, the positioning slider is connected to the positioning assembly, the push-out slider is connected to the pushing assembly, and the positioning slider and the push-out slider are connected to the push-out driving devices separately.

The push-out driving device includes a push-out motor, a push-out rack, and a push-out gear. The push-out motor is fixedly installed on the positioning bracket, the push-out gear is fixedly installed on an output shaft of the push-out motor, the push-out rack is installed on the positioning slider or the push-out slider, and the push-out gear meshes with the push-out rack.

It should be noted that, the positioning assembly further includes a droplet sensor; the droplet sensor is connected to the push-out driving device in connection with the positioning assembly, and is used for detecting the size of the reagent droplet formed at the outlet of the reagent tube connected to the reagent storage box of the storage device in the chemiluminescence immunoassay analyzer.

The specific structure of the waste liquid recycling device is as follows. The waste liquid recycling device includes a liquid collection bracket; the liquid collection bracket mainly consists of a horizontal portion and a vertical portion; the vertical portion is perpendicularly connected at a center of the horizontal portion; the horizontal portion is provided with a V-shaped first groove, the vertical portion is provided with a guide groove, and the first groove is in communication with the guide groove; the horizontal portion of the liquid collection bracket is located below the outlet of the reagent tube connected to the reagent storage box of the storage device in the chemiluminescence immunoassay analyzer, so that the reagents drip from the outlets of the reagent tubes into the first groove; the vertical portion of the liquid collection bracket is installed on the bottom plate of the chemiluminescence immunoassay analyzer, and the guide groove is in communication with a liquid collection box disposed below the bottom plate.

As a further limitation, the bottom of the vertical portion is connected to a flange, and the flange is fixed on the bottom plate of the chemiluminescence immunoassay analyzer through screws.

Preferably, reinforcing rib plates are arranged between the vertical portion and the horizontal portion, and several auxiliary holes are provided in the reinforcing rib plates.

Compared with the prior art, the present invention has the following beneficial effects.

1. The sample feeding assembly of the present invention is provided with the sample bearing cup holes in the belt, and the sample bearing cups can be directly installed on the belt, so that the samples can be continuously fed in practice and the number of fed samples is increased. During the detection, the samples can be directly put in the sample bearing cups and the belt can convey the samples into the analyzer; thereby, the samples can be tested upon arrival, the waiting time is reduced, and the detection efficiency is improved.

2. The storage device of the present invention includes the reagent storage boxes and the capillary tube storage boxes which form integrated structures. In practice, the reagent storage boxes and the capillary tube storage boxes can move with each other, a driving device is thus saved, the assemblies in the analyzer are reduced, and the volume of the analyzer is reduced. Meanwhile, in practice, the storage assemblies (the reagent storage boxes and the capillary tube storage boxes) can be added according to detection requirements. The storage assemblies can be added or removed according to actual needs, which can meet the requirements of different users. Users can select reagents according to the samples to be tested, and then combine the reagents at will. Meanwhile, the storage capacity of the capillary tubes is also increased.

More importantly, because the rubber film flaps capable of being opened or closed are disposed at the left-side through-hole and the right-side through-hole and can block the left-side through-hole and the right-side through-hole to protect the capillary tubes, maintain the humidity and cleanliness in the capillary tube storage chamber, and reduce dust entering the capillary tube storage chamber to cause contamination to the capillary tubes, thereby ensuring the accuracy of the detection results and improving the detection accuracy.

Meanwhile, the buffering pad is disposed on the side surfaces of the capillary tube storage box and the reagent storage box. When the capillary tube is to be pushed out, the capillary tube push-out device contacts the capillary tube storage box for positioning. Therefore, the buffering pad can prevent the capillary tube push-out device from colliding with the capillary tube storage box, so that the position accuracy of each part in the analyzer will not be affected by collision, the normal operation of each part in the analyzer is ensured, and the probability of failures in the analyzer is reduced.

3. The capillary tube push-out device of the present invention is mainly used for pushing the capillary tube out of the right-side through-hole in each capillary tube storage box of the storage device in the chemiluminescence immunoassay analyzer. Firstly, the positioning assembly is used for positioning. Then, the positioning rod in the positioning assembly rests on the capillary tube storage box, and the spring is compressed at the moment of the contact. The spring achieves damping and buffering effects to avoid direct collision. After the positioning, the push rod in the pushing assembly can push the capillary tube out of the capillary tube storage box more smoothly. Under the action of the spring and the buffering pad, the transmission of vibration can be reduced and the detection process is more reliable.

4. The waste liquid recycling device of the present invention can recycle the waste liquid. When the reagent droplet is formed at the outlet of the reagent tube, the droplet may drip down with a slight vibration and cause impacts in the analyzer. The waste liquid recycling device can be disposed to effectively recycle the dripping waste liquid.

BRIEF DESCRIPTION OF THE DRAWINGS

To describe the technical solutions in the embodiments of the present invention more clearly, the following briefly introduces the accompanying drawings required for describing the embodiments. It should be understood that, the accompanying drawings in the following description show merely some embodiments of the present invention, and shall not be construed as limitations to the scope of the present invention. Persons of ordinary skill in the art can derive other related drawings from these accompanying drawings without creative efforts.

DETAILED DESCRIPTION OF THE EMBODIMENTS

The present invention will be further described below with reference to the embodiments. The embodiments to be described are only a part rather than all of the embodiments of the present invention. All other embodiments derived by persons of ordinary skill in the art based on the embodiments of the present invention without creative efforts shall fall within the protection scope of the present invention.

Embodiment 1

Figure 1:
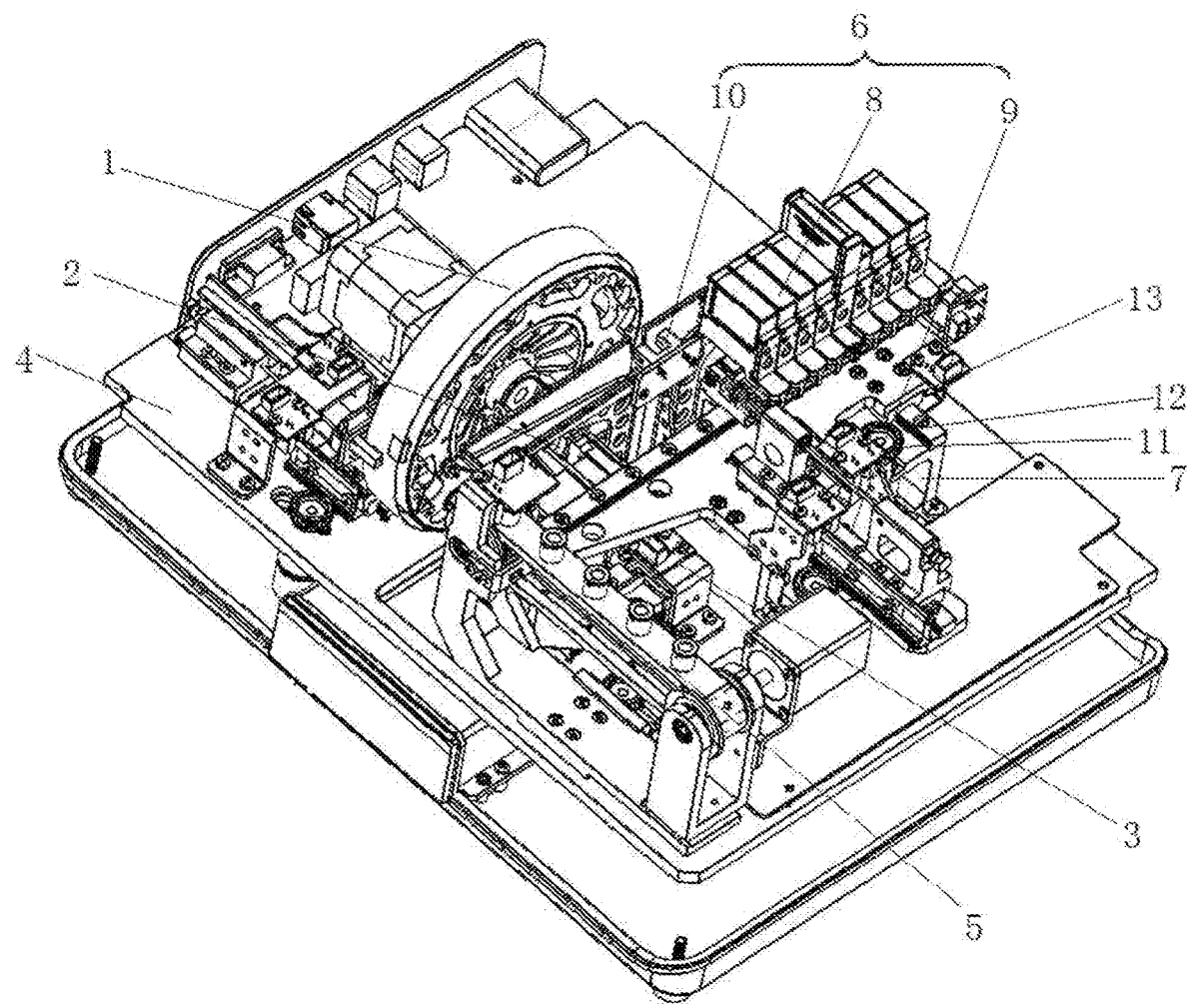
FIG. 1 is a schematic diagram of an overall structure of the present invention.
Figure 2:
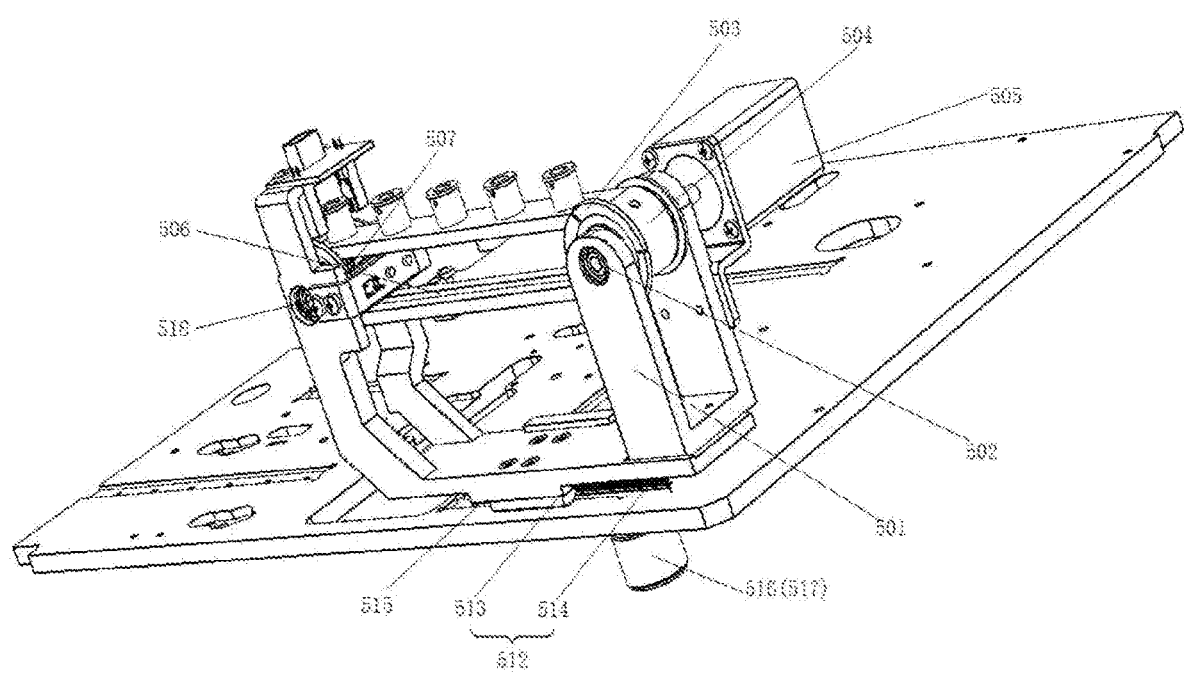
FIG. 2 is a schematic diagram of an overall structure of a sample feeding assembly according to the present invention.
Figure 3:
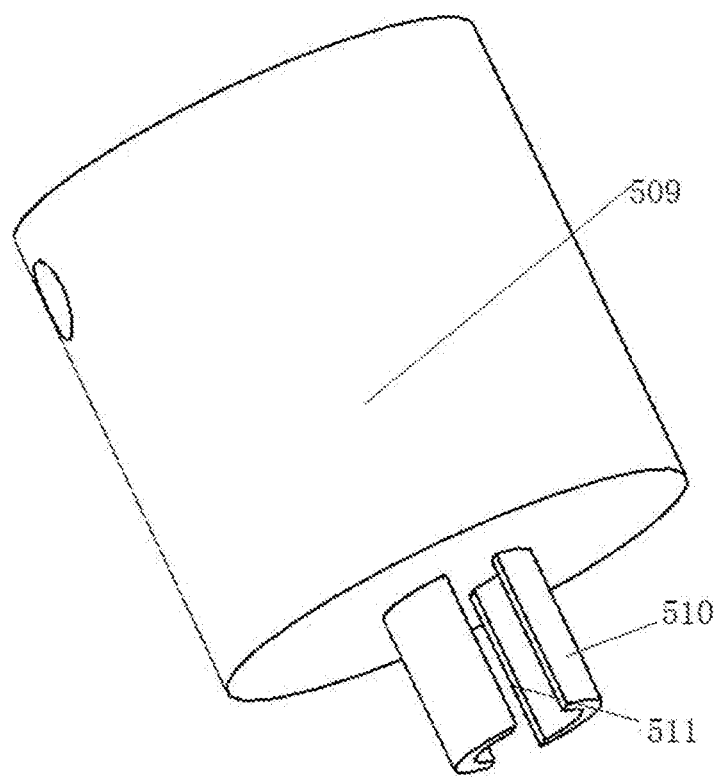
FIG. 3 is a schematic structural diagram of a sample bearing cup in the sample feeding assembly according to the present invention.
Figure 4:
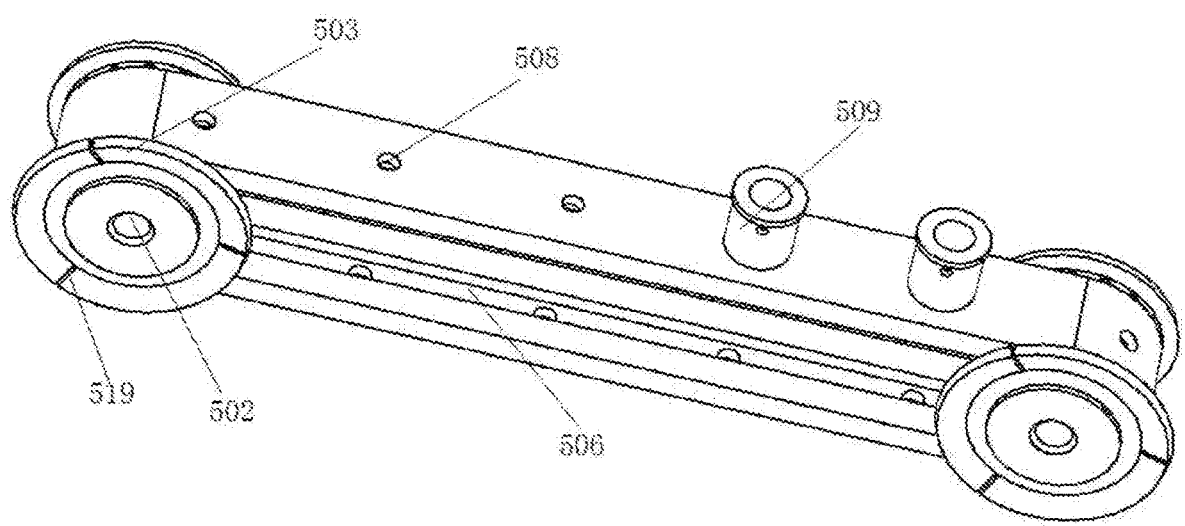
FIG. 4 is a schematic diagram illustrating connections between a belt and pulleys in the sample feeding assembly according to the present invention.
Figure 5:
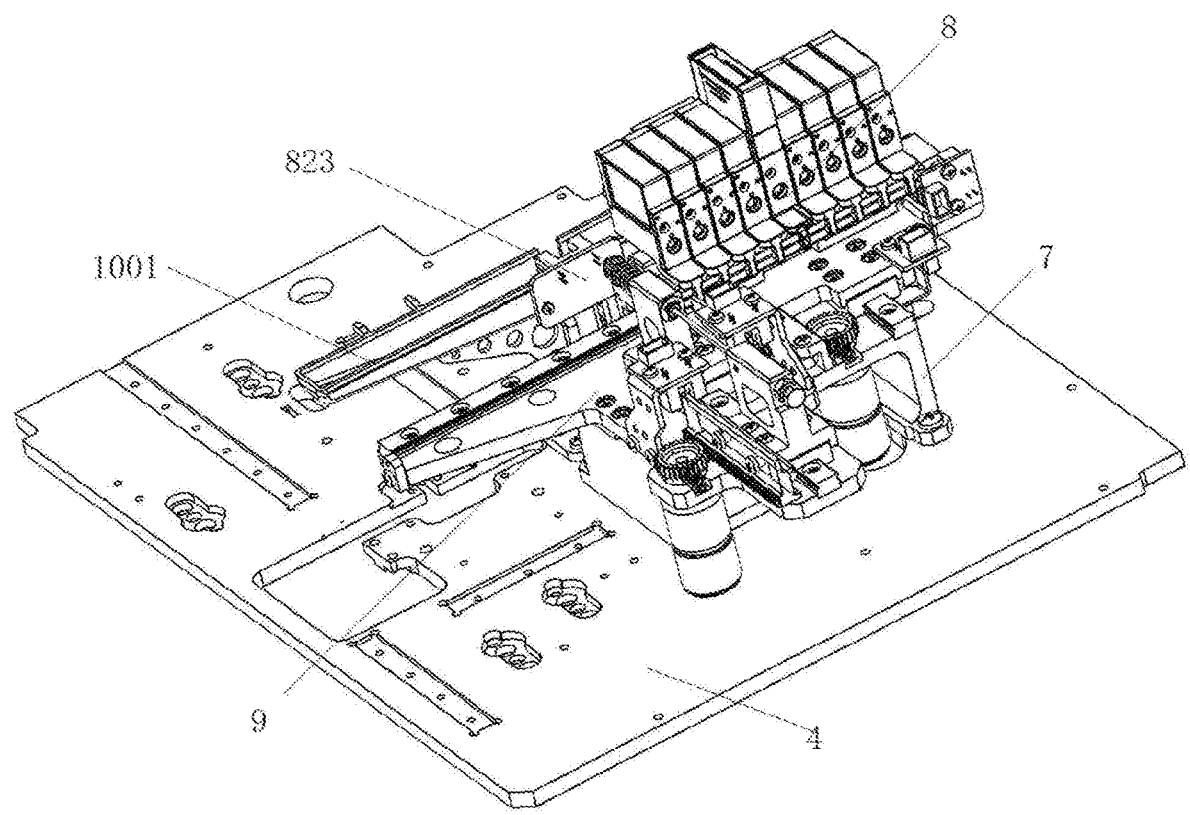
FIG. 5 is a schematic diagram of an overall structure of a charging and recycling system according to the present invention.
Figure 6:
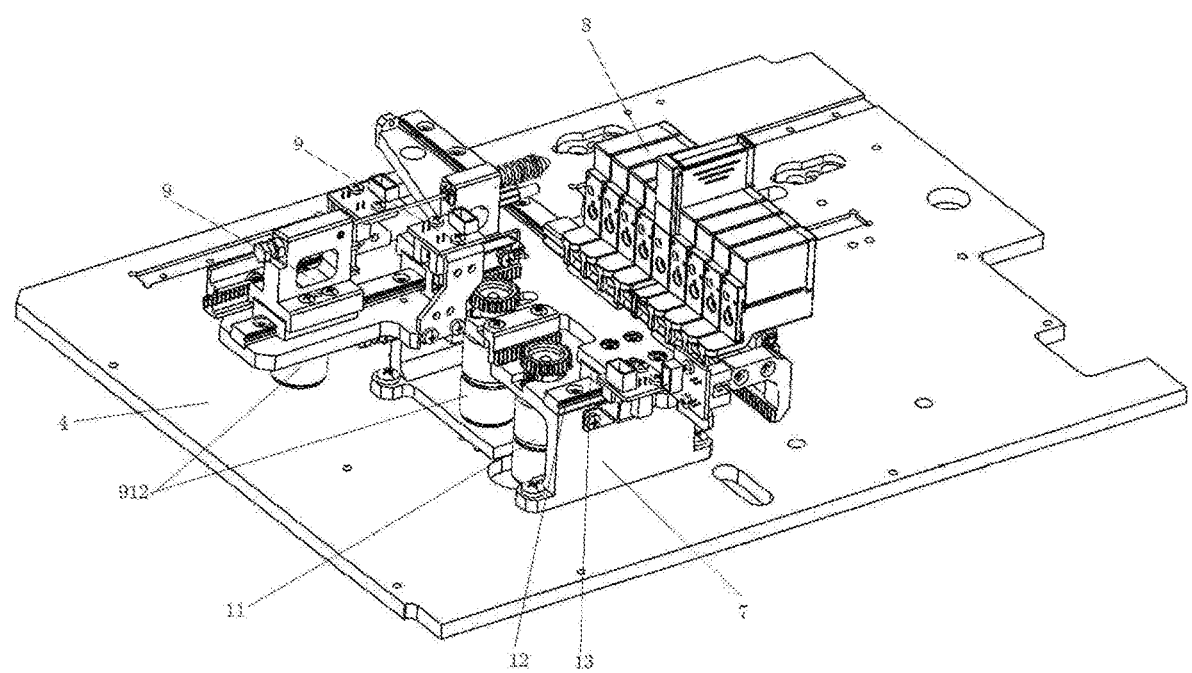
FIG. 6 is a schematic diagram of the overall structure without a waste liquid recycling device in FIG. 5 according to the present invention.
Figure 7:
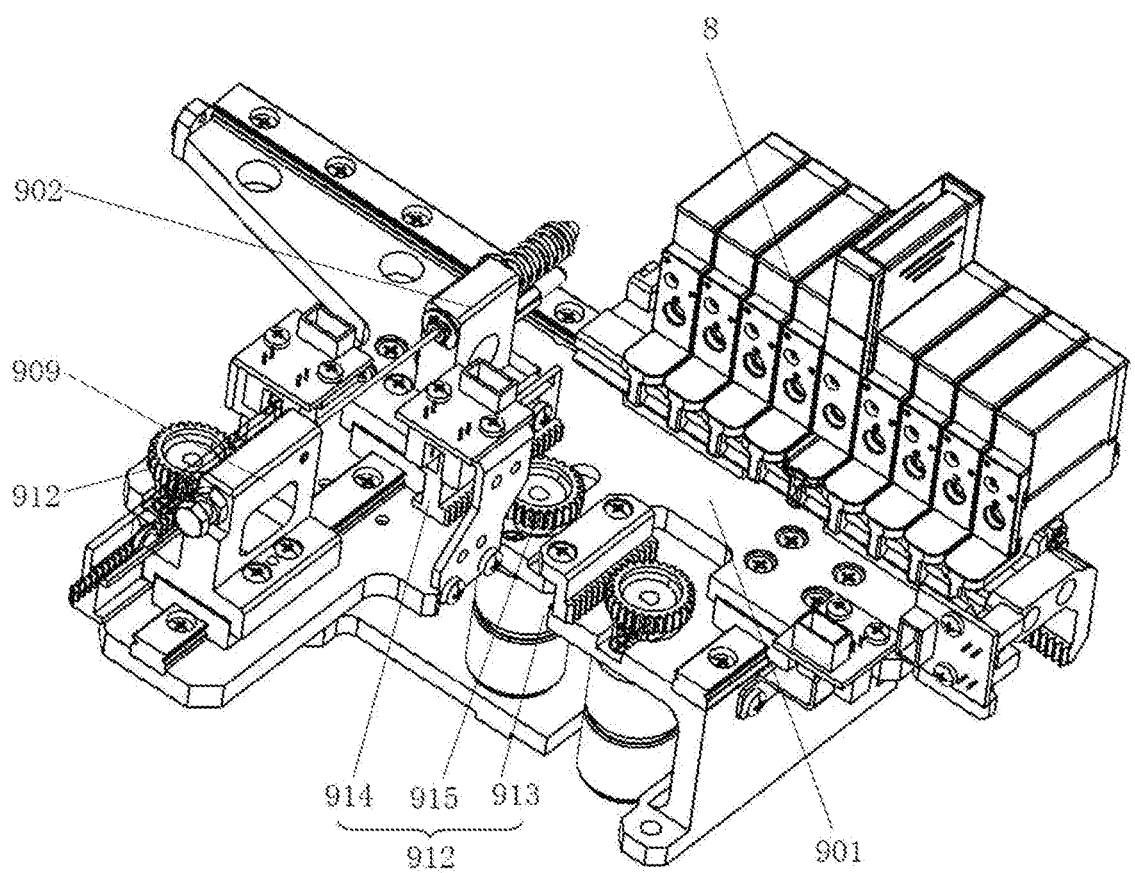
FIG. 7 is a schematic diagram illustrating positional relationships between a storage device and a capillary tube push-out device according to the present invention.
Figure 8:
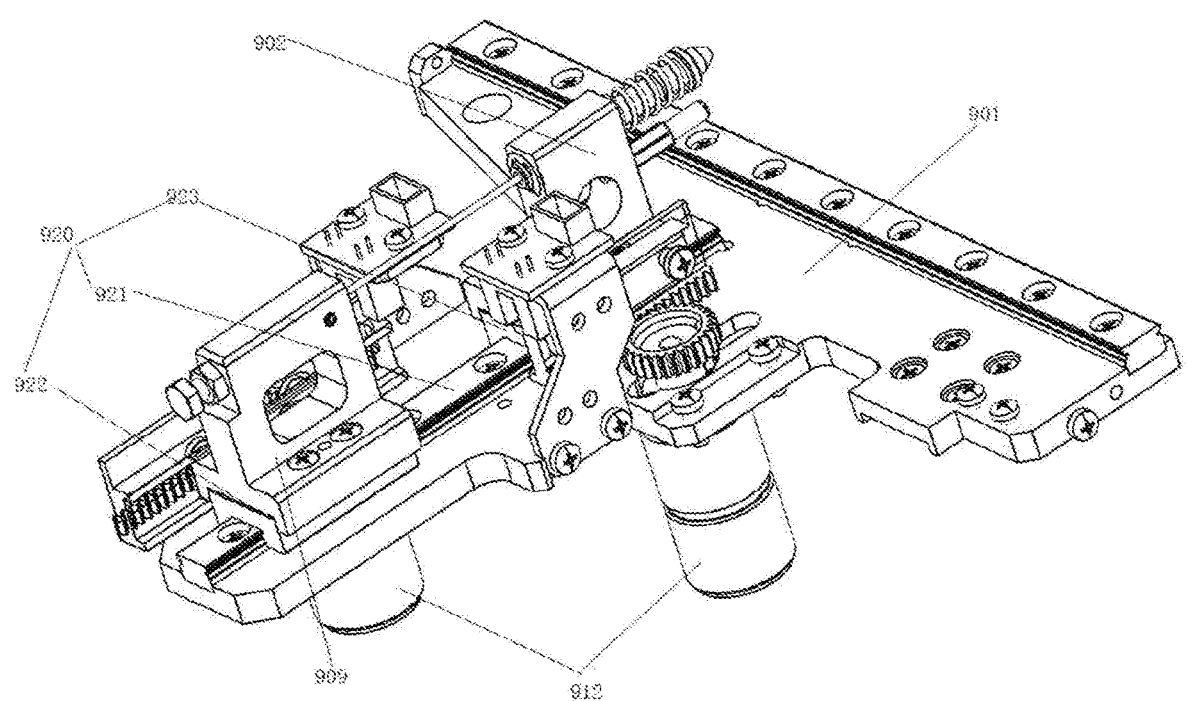
FIG. 8 is a schematic diagram of an overall structure of the capillary tube push-out device according to the present invention.
Figure 9:
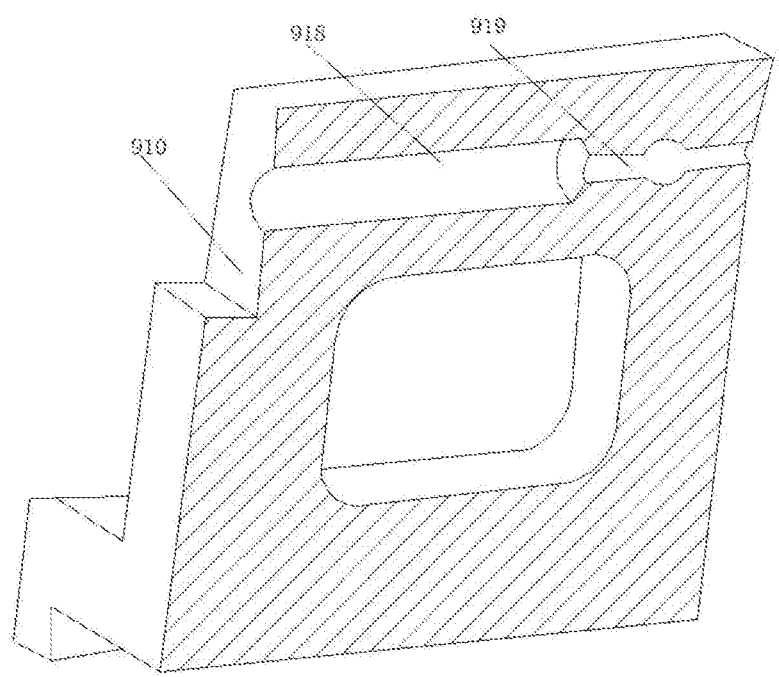
FIG. 9 is a schematic sectional view of a push rack according to the present invention.
Figure 10:
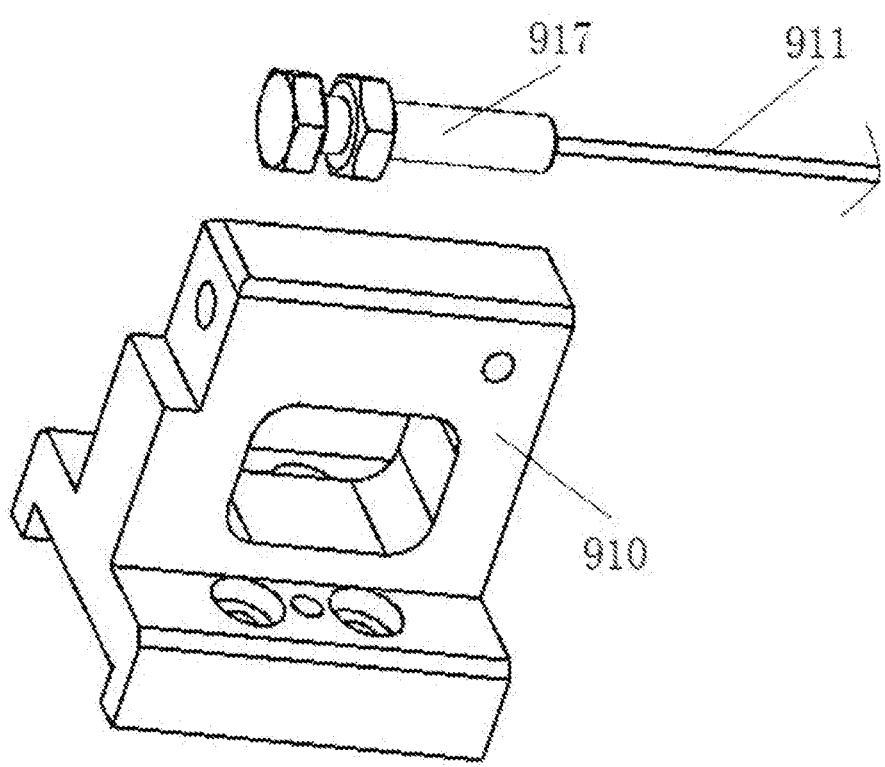
FIG. 10 is a schematic exploded diagram of a pushing assembly according to the present invention.
Figure 11:
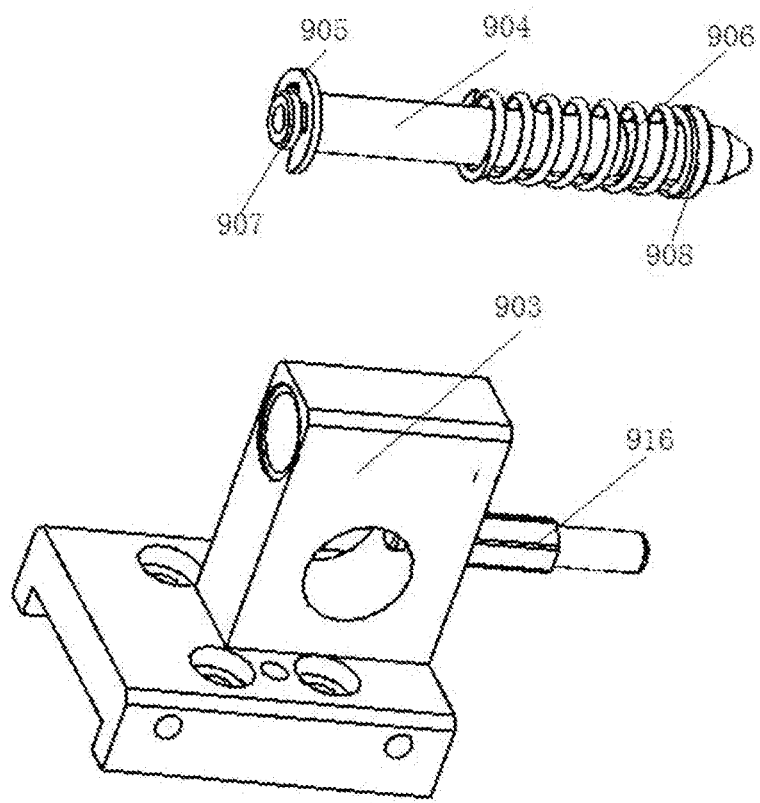
FIG. 11 is a schematic exploded diagram of a positioning assembly according to the present invention.
Figure 12:
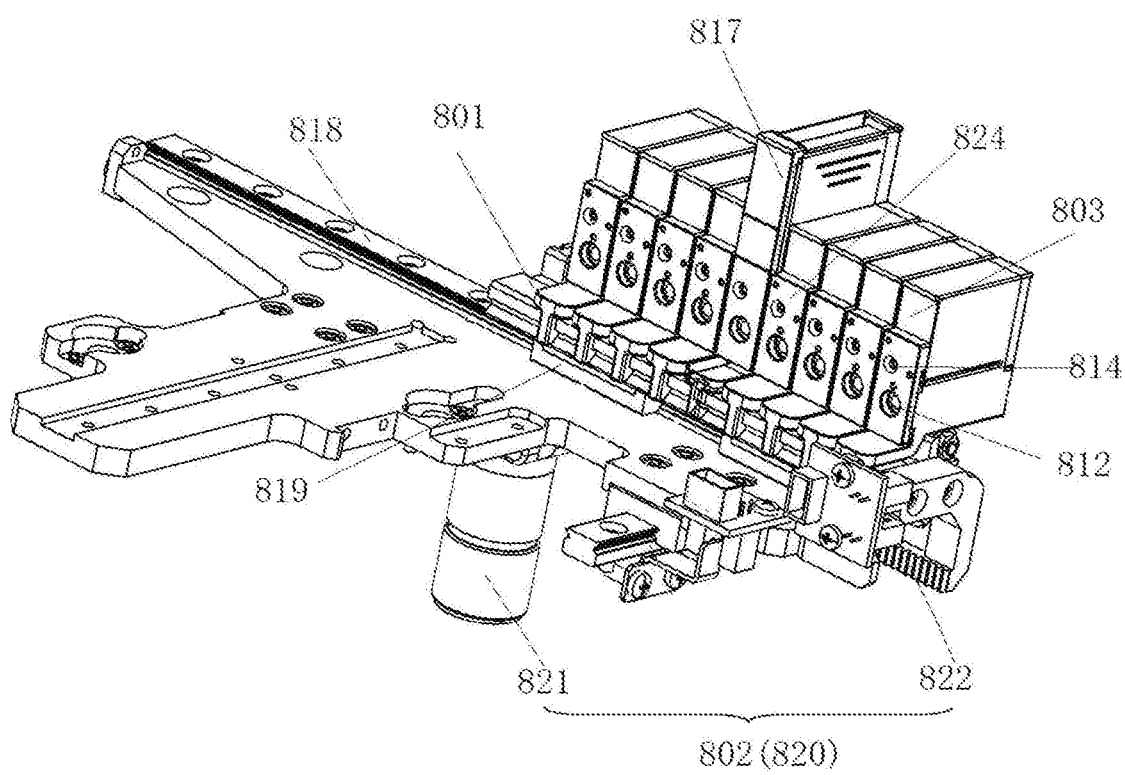
FIG. 12 is a schematic diagram of an overall structure of the storage device according to the present invention.
Figure 13:
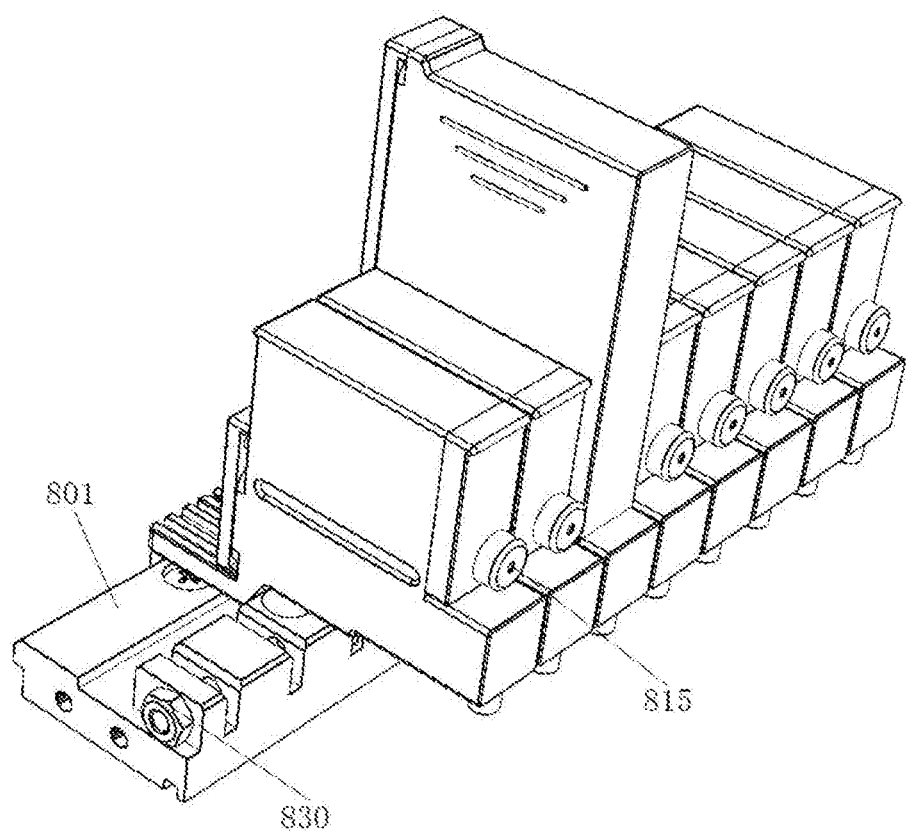
FIG. 13 is a schematic diagram illustrating positional relationships between a storage seat and storage assemblies according to the present invention.
Figure 14:
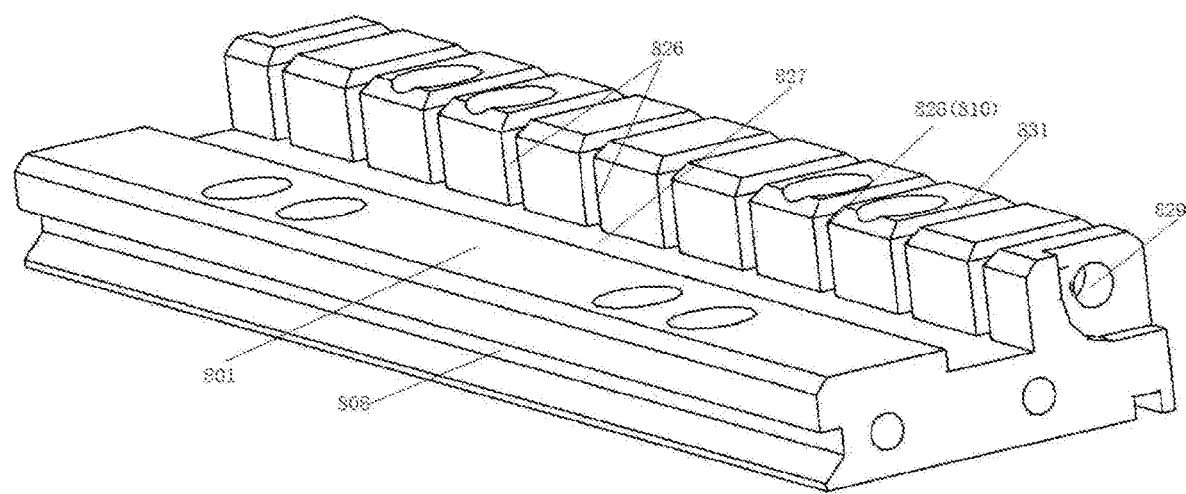
FIG. 14 is a schematic diagram of an overall structure of the storage seat according to the present invention.
Figure 15:
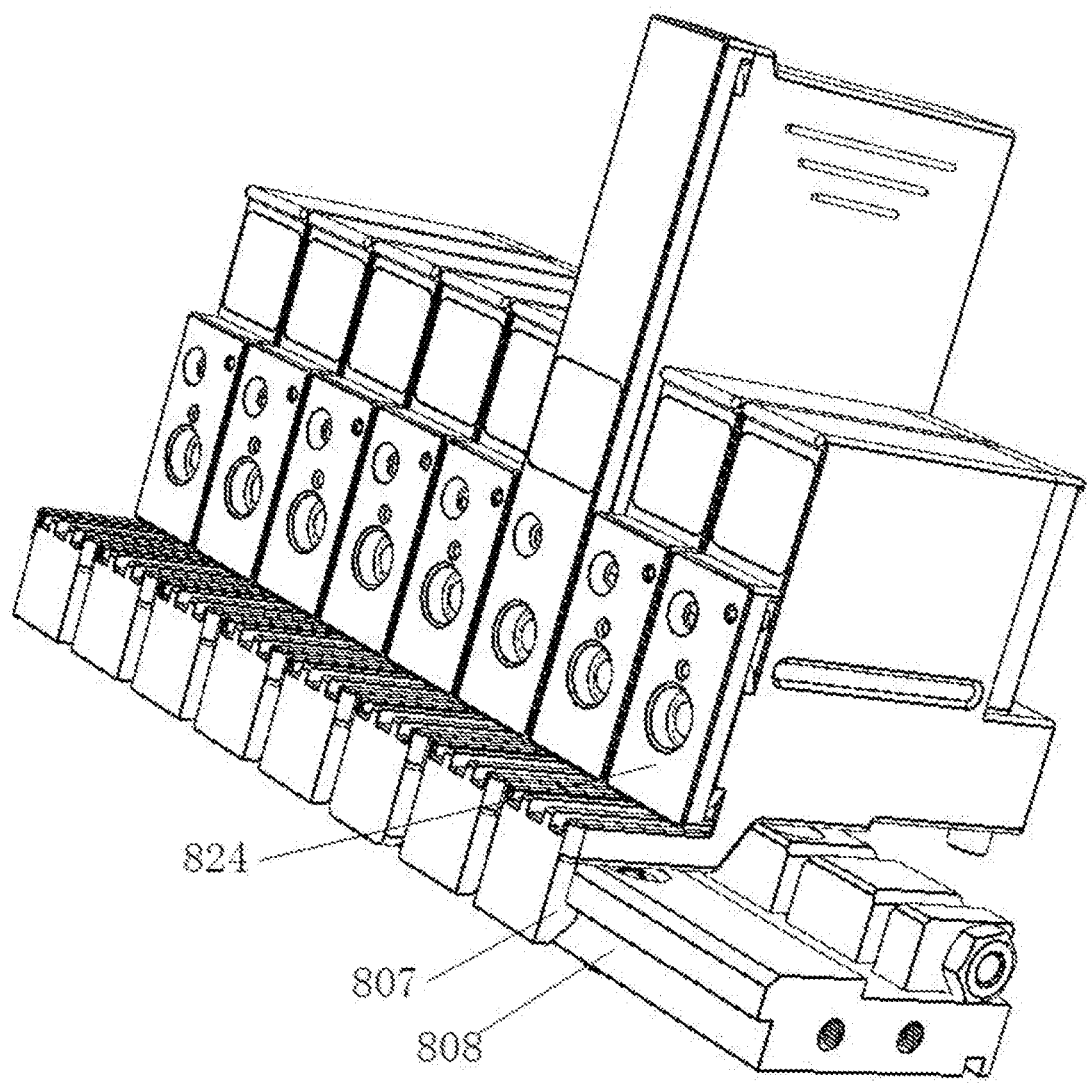
FIG. 15 is a schematic diagram of the structure on the other side in FIG. 13 according to the present invention.
Figure 16:
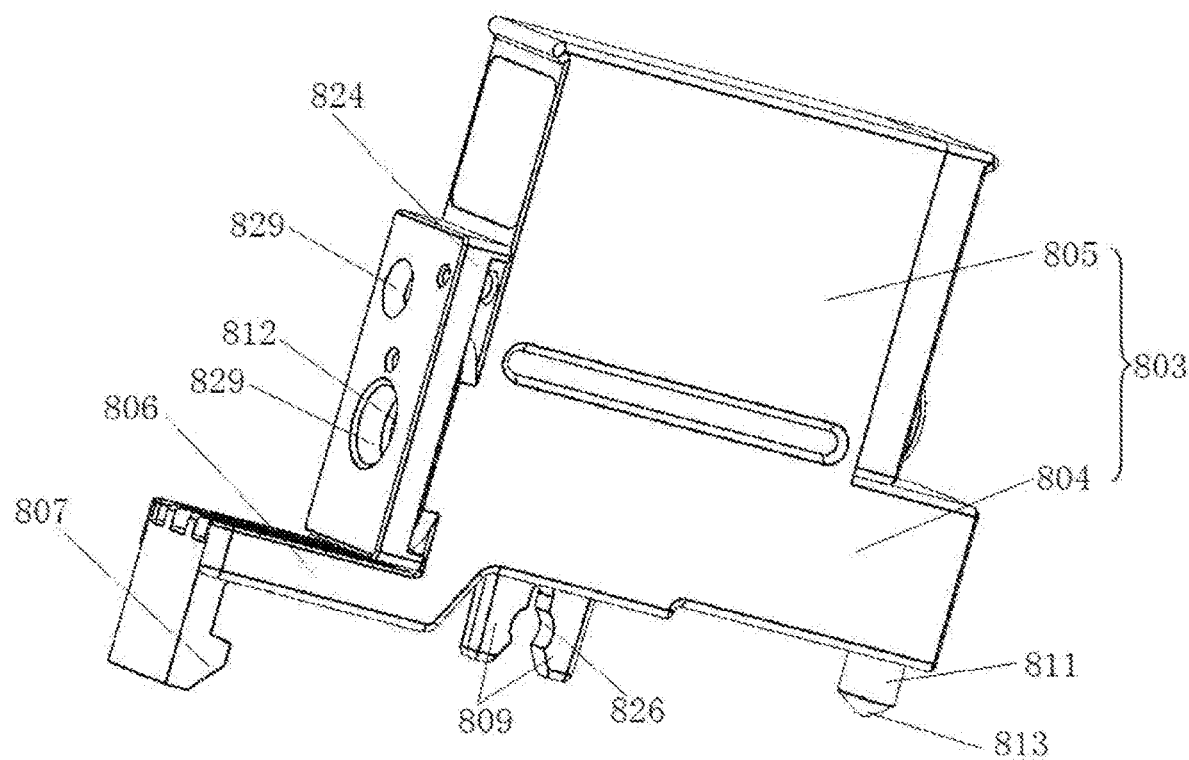
FIG. 16 is a schematic diagram of an overall structure of a storage assembly according to the present invention.
Figure 17:
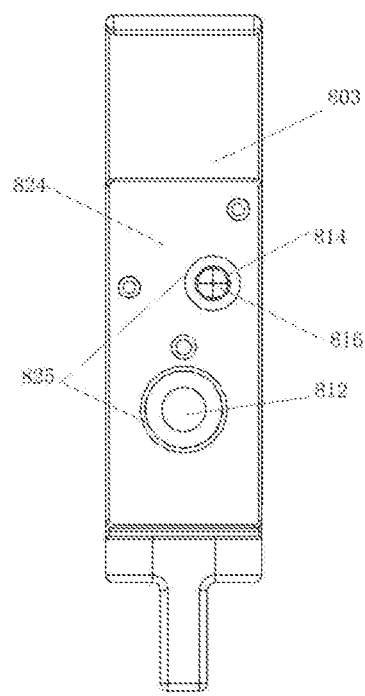
FIG. 17 is a left view of FIG. 16 according to the present invention.
Figure 18:
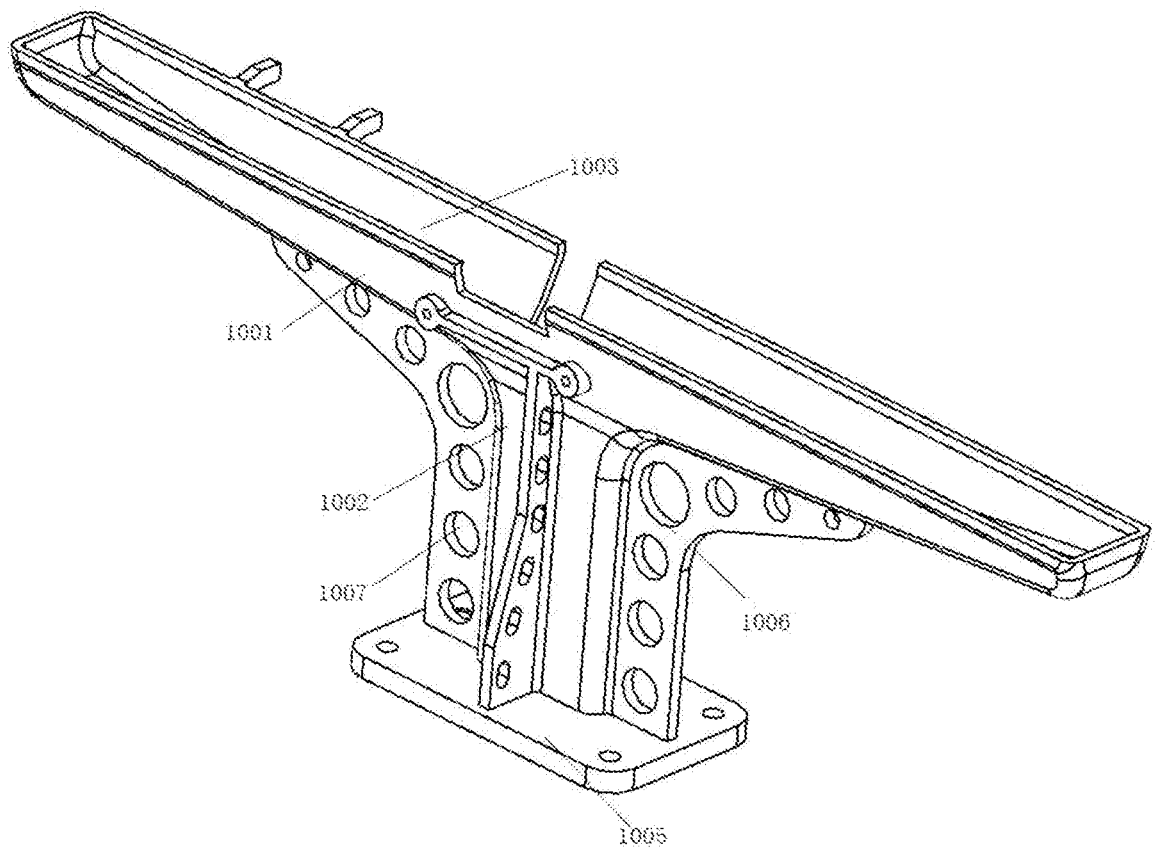
FIG. 18 is a schematic diagram of an overall structure of the waste liquid recycling device according to the present invention.
Figure 19:
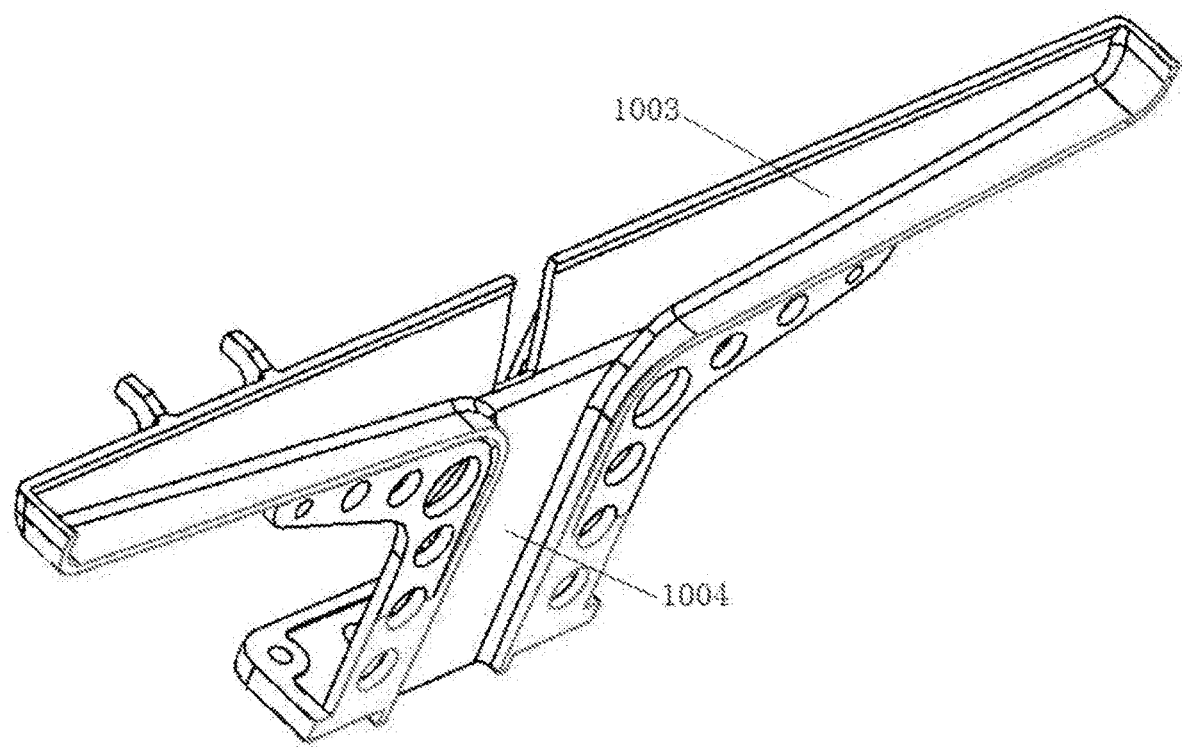
FIG. 19 is a half-sectional view of FIG. 18 according to the present invention.

Referring to FIGS. 1-19 of the specification, this embodiment discloses a chemiluminescence immunoassay analyzer, which mainly consists of the following parts:

a rotating disc assembly 1 for carrying and thermal insulation of capillary tubes;

an air-blowing assembly 2 for removing residual liquid from the capillary tubes;

a detection assembly 3 for detecting the number of luminescent photons in the capillary tubes;

a bottom plate 4 for installing the rotating disc assembly 1, the air-blowing assembly 2, and the detection assembly 3; and a charging and recycling system 6 and a sample feeding assembly 5, wherein the charging and recycling system 6 includes a fixed seat 7, a capillary tube push-out device 9, a storage device 8, a first driving device 11, and a waste liquid recycling device 10;

the storage device 8 is used for storing reagents and providing coated capillary tubes;

the capillary tube push-out device 9 is used for pushing the capillary tubes out of the storage device 8 and squeezing out the reagents stored in the storage device 8;

the sample feeding assembly 5 is used for providing samples;

the waste liquid recycling device 10 is used for recycling the reagents overflowing and dripping from the storage device 8;

the fixed seat 7 and the waste liquid recycling device 10 are fixedly installed on the bottom plate 4, the capillary tube push-out device 9 is slidably installed on the fixed seat 7 through a first guide rail 12 and a first guide block 13, the first driving device 11 is connected to the capillary tube push-out device 9 and is configured for driving the capillary tube push-out device 9 to move on the fixed seat 7, and the storage device 8 is slidably installed on the capillary tube push-out device 9 and is configured for moving on the capillary tube push-out device 9;

the waste liquid recycling device 10 is located at a central position of the bottom plate 4, the rotating disc assembly 1 is located on a left side of the waste liquid recycling device 10, and the air-blowing assembly 2, the detection assembly 3, the capillary tube push-out device 9, the storage device 8, and the sample feeding assembly 5 are located on a right side of the waste liquid recycling device 10.

In practice, the capillary tube push-out device 9 pushes the capillary tubes out of the storage device 8 and into the rotating disc assembly 1, the rotating disc assembly 1 rotates and sends the capillary tubes to the sample feeding assembly 5, the sample feeding assembly 5 sends blood samples to the capillary tubes in the rotating disc assembly 1, and the capillary tubes suck in the samples through siphonage. After incubation in the rotating disc assembly 1, the capillary tubes are sent to the air-blowing assembly 2, the air-blowing assembly 2 removes residual liquid from the capillary tubes, and the rotating disc assembly 1 sends the capillary tubes to the storage device 8. The capillary tube push-out device 9 squeezes the reagents out of the storage device 8, and after the capillary tubes suck in the reagents, the rotating disc assembly 1 sends the capillary tubes to the detection assembly 3 and pushes the capillary tubes into the detection assembly 3 for detection. After the detection is completed, the capillary tubes are sent out. Therefore, automatic detection is achieved.

It should be noted that, the rotating disc assembly 1, the air-blowing assembly 2, and the detection assembly 3 in this embodiment can be constructed with reference to those disclosed in an invention with the application number of CN201910774133.7, and the details will not be repeated herein.

The present invention is further described below through specific structures of the sample feeding assembly 5, the storage device 8, the capillary tube push-out device 9, and the waste liquid recycling device 10.

The specific structure of the sample feeding assembly 5 is as follows.

The sample feeding assembly 5 includes a bracket 501, and rotating shafts 502 are rotatably installed on left and right ends of the bracket 501, respectively. Two pulleys 503 are rotatably installed on the rotating shafts 502, respectively, and the two pulleys 503 are connected through a belt 504. A drive motor 505 is fixedly installed on a side surface of the bracket 501, and an output shaft of the drive motor 505 is connected to one of the rotating shafts 502. A groove 506 is provided on an inner side surface of the belt 504, and a depression 507 is disposed on each pulley 503 and at a position corresponding to the groove 506 on the belt 504. Several bearing holes 508 are arranged at equal intervals in the belt 504 along a length direction thereof, the bearing holes 508 are in communication with the groove 506, and a sample bearing cup 509 is arranged in each bearing hole 508. A positioning column 510 with gaps 511 is disposed on a bottom of the sample bearing cup 509, and the sample bearing cup 509 is connected to the bearing hole 508 in the belt 504 through the positioning column 510 by means of interference fit.

Therefore, in practice, the drive motor 505 drives the rotating shafts 502 to force the pulleys 503 to rotate, and the belt 504 moves accordingly. The sample bearing cups 509 are installed through the bearing holes 508, respectively. Specifically, the positioning column 510 with the gaps 511 is disposed on the bottom of each of the sample bearing cups 509, and the sample bearing cup 509 is connected to the bearing hole 508 in the belt 504 through the positioning column 510 by means of interference fit. Therefore, the sample bearing cups 509 can be placed or removed as needed in actual use, and the placing or removing process is more convenient. The sample bearing cups 509 are sequentially conveyed by the belt 504 into the analyzer and provide samples to the capillary tubes in the rotating disc assembly 1.

Since the groove 506 is provided on the inner side surface of the belt 504 and the depression 507 is disposed on each pulley 503 and at the position corresponding to the groove 506 on the belt 504, after the sample bearing cups 509 are installed, the positioning columns 510 of the sample bearing cups 509 pass through the belt 504 and enter the groove 506. Due to the gaps 511 on each positioning column 510, the sample bearing cups 509 are more stably arranged after being installed by means of interference fit. Besides, the groove 506 and the depression 507 can be provided to effectively prevent the movement of the sample bearing cups 509 from being hindered.

A bracket slidable assembly 512 below the bracket 501 is connected to a bracket driving assembly, and the bracket driving assembly is configured for driving the bracket 501 to move. Thereby, the bracket 501 is driven to move by the bracket driving assembly and is drawn closer to the capillary tubes in the rotating disc assembly 1, which facilitates siphoning of the samples from the sample bearing cups 509 into the capillary tubes.

The bracket slidable assembly 512 includes a bracket slider 513 and a bracket slide rail 514. The bracket slider 513 is installed on a bottom of the bracket 501, the bracket slide rail 514 is installed on the bottom plate 4 of the chemiluminescence immunoassay analyzer, and the bracket slider 513 cooperates with the bracket slide rail 514, so that the bracket 501 can move more stably.

Preferably, limiting protrusions 515 are disposed on two sides of the bottom of the bracket 501, an area for installing the bracket slider 513 is formed between the limiting protrusions 515, and the bracket slider 513 is installed in this area. Therefore, the installation of the bracket slider 513 is facilitated, and the bracket slider 513 can be easily positioned and more stably installed.

In this embodiment, the bracket driving assembly is a gear-rack driving assembly 516 with the following structure. The gear-rack driving assembly 516 includes a bracket gear, a bracket rack, and a bracket motor 517. The bracket motor 517 is installed on the bottom plate 4 of the chemiluminescence immunoassay analyzer, the bracket rack is installed on a side surface of the bracket 501, the bracket gear is fixedly installed on an output shaft of the bracket motor 517, and the bracket gear meshes with the bracket rack. Therefore, the bracket 501 is enabled to move through forward or reverse rotation of the bracket motor 517 under control.

It should be noted that, in addition to the gear-rack driving assembly 516, the bracket driving assembly can also be a pneumatic driving assembly, a hydraulic driving assembly, or a leadscrew driving assembly as long as it can drive the bracket 501 to move, and the details will not be repeated herein.

Preferably, the pulley 503 is a toothed pulley, the belt 504 is a toothed belt, and the depression 507 is disposed in the middle of the teeth of the toothed pulley 503. Therefore, when the pulleys 503 rotate and force the belt 504 to move, the slipping of the belt can be avoided.

Preferably, a bracket sensor 518 is installed on the bracket 501 and is close to one of the pulleys 503, detection gaps 519 are disposed on the edge of the pulley 503, and the bracket sensor 518 is connected to the drive motor 505. Therefore, through detection of the pulley 503, the bracket sensor 518 can detect the positions of the sample bearing cups 509.

Further, the specific structure of the storage device 8 is as follows.

The storage device 8 includes a storage seat 801, a translation mechanism 802, and several storage assemblies 803. The translation mechanism 802 is used for driving the storage seat 801 to move. The storage assemblies 803 are arranged side by side on the storage seat 801 and each mainly consist of a reagent storage box 804 and a capillary tube storage box 805 connected above the reagent storage box 804. The reagent storage box 804 is used for storing reagents, and the capillary tube storage box 805 is used for storing coated capillary tubes. An L-shaped installation portion 806 is connected on a side surface of the reagent storage box 804, a hook 807 is disposed on the L-shaped installation portion 806, a slot 808 is provided on a side surface of the storage seat 801, and the hook 807 is configured for being engaged with the slot 808. Two positioning protrusions 809 are disposed on a bottom surface of the reagent storage box 804 and are each provided with a limiting slot 826. A bolt clamping area is formed between the two limiting slots 826. A transverse groove 827 is disposed on the storage seat 801 and divides the storage seat 801 into a left part and a right part, and the left part is lower than the right part. Several separating grooves 828 are disposed in the right part. The separating grooves 828 are in communication with the transverse groove 827 and divide the right part into several bumps 831. Each separating groove 828 between the bumps 831 forms a positioning protrusion installation area 810, a through-hole 829 is provided on a side surface of each bump 831, and after the hook 807 of the L-shaped installation portion 806 is engaged with the slot 808, the two positioning protrusions 809 are located in the positioning protrusion installation area 810 and are limited by a bolt 830 passing through the through-holes 829 in the bumps 831; therefore, the storage assembly 803 is fixed on the storage seat 801.

In view of the above, the storage assemblies 803 can each be used for storing capillary tubes and reagents and can move by means of one common translation mechanism 802, so that the number of the driving devices required is reduced and the volume of the analyzer can be effectively reduced. The hook 807 of the reagent storage box 804 is engaged with the slot 808 on the side surface of the storage seat 801, the two positioning protrusions 809 are disposed on the bottom surface of the reagent storage box 804, the area for clamping the bolt 830 is formed between the positioning protrusions 809, and the two positioning protrusions 809 are located in the positioning protrusion installation area 810 and are limited by the bolt 830 passing through the through-holes 829 in the bumps 831; therefore, the storage assembly is fixed on the storage seat 801. In practice, the storage assemblies 803 can be installed or removed according to specific conditions of the samples, and the required reagents are placed in the reagent storage boxes 804, so that free combinations of the reagents can be realized and the application scope of the present invention is expanded.

As a further limitation, a reagent chamber is formed inside the reagent storage box 804, a reagent tube 811 is disposed on a side wall of the reagent storage box 804, the reagent tube 811 is in communication with the reagent chamber, and a rubber film 812 is disposed on a side wall of the reagent storage box 804 opposite to the reagent tube 811. When the rubber film 812 is pressed, the reagents in the reagent chamber flow out of the reagent tube 811 and a reagent droplet 813 is formed at an outlet of the reagent tube 811.

A capillary tube storage chamber is formed through partition plates in the capillary tube storage box 805. The capillary tube storage chamber is wider than a diameter of the capillary tube by 0.5-1 mm, and several capillary tubes are vertically stacked in order inside the capillary tube storage chamber. A left-side through-hole 814 and a right-side through-hole 815 are respectively disposed on a left side and a right side at a bottom of the capillary tube storage box 805. The left-side through-hole 814 and the right-side through-hole 815 are both in communication with the capillary tube storage chamber. Rubber film flaps 816 capable of being opened or closed are disposed at the left-side through-hole 814 and the right-side through-hole 815.

In this embodiment, the capillary tube storage chamber is wider than the diameter of the capillary tube by 0.7 mm.

In view of the above, in practice, by pressing the rubber film 812, the reagent droplet 813 is formed at the outlet of the reagent tube 811 and the reagents are provided to the capillary tube. The rubber film flaps 816 can seal the capillary tube storage chamber to maintain a relatively stable state inside the capillary tube storage chamber. After the rubber film flaps 816 are closed, air or dust cannot enter the capillary tube storage chamber from the outside, so that the influence of external factors on the detection results can be effectively reduced and the accuracy of the detection results can be effectively improved.

Preferably, the center of the rubber film flap 816 has cross-shaped, Y-shaped, and X-shaped scratches, so that the rubber film flap 816 can be closed after the capillary tube gets in or out, the capillary tube can be pushed out more smoothly without being hindered, and the sealing effect can be ensured after the capillary tube is pushed out.

A cleaning liquid tank 817 is installed on the storage seat 801.

It should be noted that, the translation mechanism 802 is a pneumatic translation mechanism, a hydraulic translation mechanism, a gear-rack translation mechanism, a leadscrew translation mechanism, or an electric push-rod translation mechanism, as long as it can push the storage seat 801 to move.

In practice, the storage seat 801 is slidably installed on the capillary tube push-out device 9 through a slide rail 818 and a slider 819. The translation mechanism 802 forces the storage seat 801 to move on the capillary tube push-out device 9. In this embodiment, the translation mechanism 802 is a gear-rack translation mechanism. The gear-rack translation mechanism 820 includes a translation motor 821, a translation gear, and a translation rack 822. The translation motor 821 is fixedly installed on the capillary tube push-out device 9, the translation rack 822 is fixedly installed on the storage seat 801, the translation gear is installed on the translation motor 821 and meshes with the translation rack, and the translation motor 821 rotates to force the storage seat 801 to move.

In practice, the translation mechanism 802 is connected to a detection sensor 823, the detection sensor 823 is used for detecting the positions of the storage assemblies 803, and the translation mechanism 802 starts or stops according to information fed back by the detection sensor 823.

Preferably, in this embodiment, a buffering pad 824 is disposed on side surfaces of the capillary tube storage box 805 and the reagent storage box 804, a circular hole 825 is provided in the buffering pad 824, and the position of the circular hole 825 is corresponding to those of the left-side through-hole 814 and the rubber film flap 816.

The buffering pad 824 provides a good buffering effect, which prevents the capillary tube push-out device 9 from colliding with the storage assembly 803 during the positioning process when the capillary tube is pushed out.

Further, the specific structure of the capillary tube push-out device 9 is as follows.

The capillary tube push-out device 9 includes a positioning bracket 901, a positioning assembly 902, and a pushing assembly 909. The positioning bracket 901 is slidably installed on the fixed seat 7, the positioning assembly 902 and the pushing assembly 909 are slidably installed on the positioning bracket 901, and the positioning assembly 902 is located in front of the pushing assembly 909. The positioning assembly 902 and the pushing assembly 909 are each connected to a push-out driving device 912, and the push-out driving devices 912 are configured for driving the positioning assembly 902 and the pushing assembly 909 to move on the positioning bracket 901 separately. The positioning assembly 902 is connected to a press rod 916. The press rod 916 is used for pressing the rubber film 812 on each reagent storage box 804 of the storage device 8 in the chemiluminescence immunoassay analyzer. The positioning assembly 902 is used for positioning the left-side through-hole 814 in each capillary tube storage box 805 of the storage device 8 in the chemiluminescence immunoassay analyzer. The pushing assembly 909 is used for pushing the capillary tube out of the right-side through-hole 815 in each capillary tube storage box 805 of the storage device 8 in the chemiluminescence immunoassay analyzer.

In practice, the storage seat 801 is slidably installed on the positioning bracket 901 through the slide rail 818 and the slider 819. The translation mechanism 802 forces the storage seat 801 to move on the positioning bracket 901, so that one of the storage assemblies 803 is aligned with the positioning assembly 902. The right-side through-hole 815 of the storage assembly 803 is aligned with the rotating disc assembly 1, and the left-side through-hole 814 is aligned with the positioning assembly 902. The push-out driving device 912 connected to the positioning assembly 902 drives the positioning assembly 902 to be aligned with the storage assembly 803. Then, the push-out driving device 912 connected to the pushing assembly 909 drives the pushing assembly 909 to push the capillary tube in the capillary tube storage box 805 of the storage assembly 803 into the rotating disc assembly 1.

The first driving device 11 drives the positioning bracket 901 to move on the fixed seat 7, and the storage device 8 is drawn closer to or away from the rotating disc assembly 1.

Specifically, the positioning assembly 902 includes a positioning rack 903, a positioning rod 904, a blocking plate 905, and a spring 906. The positioning rack 903 is connected to one of the push-out driving devices 912, and the push-out driving device 912 is used for driving the positioning rack 903 to move. The positioning rod 904 is hollow inside, one end of the positioning rod 904 is tapered and the other end thereof is provided with a first limiting boss 907, and the tapered end of the positioning rod 904 is provided with a second limiting boss 908. The positioning rod 904 is slidably installed on the positioning rack 903 and has the two ends extending out of the positioning rack 903. The spring 906 and the blocking plate 905 are both sleeved on the positioning rod 904, the blocking plate 905 is close to the first limiting boss 907, and the spring 906 is close to the second limiting boss 908. Under the action of the spring 906, the first limiting boss 907 presses the blocking plate 905 on a side surface of the positioning rack 903. A push rod 911 in the pushing assembly 909 is configured for passing through the positioning rod 904 to push the capillary tube. The press rod 916 is installed on the positioning rack 903, and the press rod 916 is shorter than the positioning rod 904 extending from the right end of the positioning rack 903.

Therefore, in practice, the push-out driving device 912 drives the positioning rack 903 to move, the positioning rack 903 forces the positioning rod 904 to move, and the positioning rod 904 is drawn closer to the capillary tube storage box 805 of the storage assembly 803, till the end of the positioning rod 904 is aligned with and contacts the left-side through-hole 814 in the capillary tube storage box 805. In this case, after the positioning rod 904 contacts the capillary tube storage box 805, the positioning rod 904 compresses the spring 906, and the buffering effect is achieved through deformation of the spring 906. After the positioning, the push-out driving device 912 stops and the pushing assembly 909 pushes out the capillary tube.

As a further limitation, the pushing assembly 909 includes a push rack 910 and the push rod 911. The push rack 910 is connected to the other push-out driving device 912, and the push-out driving device 912 is configured for driving the push rack 910 to move. One end of the push rod 911 is connected to the push rack 910 and the other end thereof extends into the positioning rod 904 and then out of the positioning rod 904.

After the positioning of the positioning rod 904, the push-out driving device 912 connected to the pushing assembly 909 drives the push rack 910 to move, and the push rack 910 forces the push rod 911 to move. The end of the push rod passes through the positioning rod 904 and extends into the capillary tube storage chamber in the capillary tube storage box 805, so that the capillary tube is pushed out of the capillary tube storage chamber and into the rotating disc assembly 1. After pushing the capillary tube into the rotating disc assembly 1, the push rod 911 moves backward, and then the positioning rod 904 moves backward. The positioning and push-out steps are completed.

Therefore, the positioning rod 904 can be used for not only positioning, but also supporting and guiding the push rod 911 to prevent the push rod 911 from breaking while pushing the capillary tube, thereby protecting the push rod 911.

Preferably, the pushing assembly 909 further includes an adjustment bolt 917, a threaded hole 918 and a guide hole 919 are provided in the push rack 910, the threaded hole 918 is in communication with the guide hole 919, and the adjustment bolt 917 matches with the threaded hole 918. The push rod 911 is connected to the push rack 910 through the adjustment bolt 917. One end of the push rod 911 passes through the guide hole 919 and is fixedly connected to an end of the adjustment bolt 917 and the other end thereof extends into the positioning rod 904. After the positioning rack 903 moves, the push rod 911 extends out of the positioning rod 904, and thereby, the adjustment bolt 917 can be turned to slightly adjust the push rod 911.

Further, the positioning assembly 902 and the pushing assembly 909 are connected to the two push-out driving devices 912 through a sliding assembly 920 separately. The sliding assembly 920 includes a sliding guide rail 921, a positioning slider 922, and a push-out slider 923. The sliding guide rail 921 is fixedly installed on the positioning bracket 901, the positioning slider 922 and the push-out slider 923 are slidably arranged on the sliding guide rail 921, the positioning slider 922 is connected to the positioning assembly 902, the push-out slider 923 is connected to the pushing assembly 909, and the positioning slider 922 and the push-out slider 923 are connected to the push-out driving devices 912 separately. Therefore, the positioning rack 903 and the push rack 910 can move more stably.

The push-out driving device 912 includes a push-out motor 913, a push-out rack 914, and a push-out gear 915. The push-out motor 913 is fixedly installed on the positioning bracket 901, the push-out gear 915 is fixedly installed on an output shaft of the push-out motor 913, the push-out rack 914 is installed on the positioning slider 922 or the push-out slider 923, and the push-out gear 915 meshes with the push-out rack 914.

It should be noted that, the positioning assembly 902 further includes a droplet sensor. The droplet sensor is connected to the push-out driving device 912 in connection with the positioning assembly 902, and is used for detecting the size of the reagent droplet 813 formed at the outlet of the reagent tube 811 connected to each reagent storage box 804 of the storage device 8 in the chemiluminescence immunoassay analyzer. Therefore, in practice, the size of the reagent droplet 813 is detected using the droplet sensor, and the push-out driving device 912 connected to the positioning assembly 902 drives the positioning rack 903 to move according to the information detected by the droplet sensor. If the size of the reagent droplet 813 is too small, the driving device drives the positioning assembly 902 to move and make the press rod 916 continuously press the rubber film 812, so that the reagent droplet 813 is enlarged. It is ensured that the squeezed reagent droplet 813 is of an appropriate size, and the waste of the reagents is avoided.

Further, the specific structure of the waste liquid recycling device 10 is as follows.

The waste liquid recycling device 10 is a liquid collection bracket 501. The liquid collection bracket 501 mainly consists of a horizontal portion 1001 and a vertical portion 1002. The vertical portion 1002 is perpendicularly connected at a center of the horizontal portion 1001. The horizontal portion 1001 is provided with a V-shaped first groove 1003, the vertical portion 1002 is provided with a guide groove 1004, and the first groove 1003 is in communication with the guide groove 1004. The horizontal portion 1001 of the liquid collection bracket 501 is located below the outlets of the reagent tubes 811 connected to the reagent storage boxes 804 of the storage device 8 in the chemiluminescence immunoassay analyzer, so that the reagents drip from the outlets of the reagent tubes 811 into the first groove 1003. The vertical portion 1002 of the liquid collection bracket 501 is installed on the bottom plate 4 of the chemiluminescence immunoassay analyzer, and the guide groove 1004 is in communication with a liquid collection box disposed below the bottom plate 4.

As a further limitation, the bottom of the vertical portion 1002 is connected to a flange 1005, and the flange 1005 is fixed on the bottom plate 4 of the chemiluminescence immunoassay analyzer through screws.

Preferably, reinforcing rib plates 1006 are arranged between the vertical portion 1002 and the horizontal portion 1001, and several auxiliary holes 1007 are provided in the reinforcing rib plates 1006.

Therefore, in practice, the overflowing reagent droplet 813 is effectively prevented from falling on the bottom plate 4 and is recycled through the waste liquid recycling device 10, so that the analyzer is kept clean inside and the impact on the detection results is reduced.

It should be noted that, in practice, during detection, the capillary tube needs to be pushed from the rotating disc assembly 1 into the detection assembly 3, and another capillary tube push-out device 9 can be disposed on the bottom plate 4 for pushing the capillary tube. Certainly, in practice, any other pushing device can also be adopted, as long as it can push the capillary tube from the rotating disc assembly 1 into the detection assembly 3.

Although the preferred embodiments of the present invention have been described, persons skilled in the art can make additional changes and modifications to these embodiments once they learn the basic creative concepts. Therefore, the appended claims are intended to be interpreted as including the preferred embodiments and all changes and modifications falling within the scope of the present invention. The above descriptions are only the preferred embodiments of the present invention and are not intended to limit the present invention. It should be pointed out that any modification, equivalent replacement, and improvement made within the spirit and principle of the present invention shall fall within the protection scope of the present invention.

What is claimed is:

1. A chemiluminescence immunoassay analyzer, comprising a bottom plate, a rotating disc assembly, an air-blowing assembly, and a detection assembly which are disposed on the bottom plate, wherein the air-blowing assembly and the detection assembly are disposed beside the rotating disc assembly, the detection assembly being configured to detect a number of luminescent photons from capillary tubes, and wherein the rotating disc assembly sends the capillary tubes to the detection assembly and pushes the capillary tubes into the detection assembly for detection; wherein the analyzer further comprises a charging and recycling system and a sample feeding assembly, wherein the charging and recycling system comprises a fixed seat, a capillary tube push-out device, a storage device, a first driving device, and a waste liquid recycling device;

the fixed seat is fixed on the bottom plate, the capillary tube push-out device is slidably disposed on the fixed seat, the first driving device is connected to the capillary tube push-out device and is configured for driving the capillary tube push-out device to move on the fixed seat, the capillary tube push-out device comprises a positioning bracket, a positioning assembly, a pushing assembly and a press rod, the positioning bracket is slidably disposed on the fixed seat, the positioning assembly and the pushing assembly are slidably disposed on the positioning bracket, the positioning assembly is connected to the press rod, the storage device comprises a storage seat slidably disposed on the positioning bracket of the capillary tube push-out device so as to move on the capillary tube push-out device, reagents are stored in the storage device and the capillary tubes which are coated are provided in the storage device, the storage device is disposed beside the rotating disc assembly, the pushing assembly of the capillary tube push-out device is disposed beside the storage device so as to push the capillary tubes from the storage device to the rotating disc assembly, the press rod of the capillary tube push-out device is movably disposed beside the storage device and faces toward the storage device so that the press rod is configured to squeeze out the reagents stored in a reagent storage box of the storage device, wherein the reagent storage box comprises a rubber film to be pressed by the press rod for squeezing out the reagents through an outlet of the reagent storage box and into a capillary tube;

the sample feeding assembly is disposed on the bottom plate and located beside the storage device, the sample feeding assembly provides samples to the capillary tubes in the rotating disc assembly;

the waste liquid recycling device is fixed on the bottom plate and located below the storage device along a gravity direction so as to recycle-the reagents overflowing and dripping from the storage device.

2. The chemiluminescence immunoassay analyzer according to claim 1, wherein the sample feeding assembly comprises a bracket, and rotating shafts are rotatably installed on first and second ends of the bracket, respectively; two pulleys are rotatably installed on the rotating shafts, respectively, and the two pulleys are connected through a belt; a drive motor is fixedly installed on a side surface of the bracket, and an output shaft of the drive motor is connected to one of the rotating shafts; a groove is provided on an inner side surface of the belt, and a depression is disposed on each of the two pulleys and at a position corresponding to the groove on the belt;

several bearing holes are arranged at equal intervals in the belt along a length direction of the belt, the bearing holes are in communication with the groove, and a sample bearing cup is arranged in each of the bearing holes; a positioning column with gaps is disposed on a bottom of the sample bearing cup, and the sample bearing cup is connected to the corresponding bearing hole in the belt through the positioning column by means of interference fit.

3. The chemiluminescence immunoassay analyzer according to claim 2, wherein a bracket slidable assembly below the bracket is connected to a bracket driving assembly, and the bracket driving assembly is configured for driving the bracket to move; the bracket slidable assembly comprises a bracket slider and a bracket slide rail, the bracket slider is installed on a bottom of the bracket, the bracket slide rail is installed on the bottom plate of the chemiluminescence immunoassay analyzer, and the bracket slider cooperates with the bracket slide rail.

4. The chemiluminescence immunoassay analyzer according to claim 1, wherein the storage device comprises a translation mechanism, and several storage assemblies; the translation mechanism is used for driving the storage seat to move; the storage assemblies are arranged side by side on the storage seat and each comprises a reagent storage box and a capillary tube storage box connected above the reagent storage box; the reagent storage box is used for storing a respective one of the reagents, and the capillary tube storage box is used for storing the capillary tubes which are coated;

an L-shaped installation portion is connected on a side surface of the reagent storage box, a hook is disposed on the L-shaped installation portion, a slot is provided on a side surface of the storage seat, and the hook is configured for being engaged with the slot; two positioning protrusions are disposed on a bottom surface of the reagent storage box and are respectively provided with two limiting slots; a bolt clamping area is formed between the two limiting slots; a transverse groove is disposed on the storage seat and divides the storage seat into a first part and a second part, and the first part is lower than the second part; several separating grooves are disposed in the second part, and the separating grooves are in communication with the transverse groove and divide the second part into several bumps; each of the separating grooves between the bumps forms a positioning protrusion installation area, through-holes are respectively provided on side surfaces of the bumps, and after the hook of the L-shaped installation portion is engaged with the slot, the two positioning protrusions are located in the positioning protrusion installation area and are limited by a bolt passing through the through-holes in the bumps; therefore, the storage assembly is fixed on the storage seat; and a cleaning liquid tank is installed on the storage seat.

5. The chemiluminescence immunoassay analyzer according to claim 4, wherein a reagent chamber is formed inside the reagent storage box, a reagent tube is disposed on a side wall of the reagent storage box, the reagent tube is in communication with the reagent chamber, and a rubber film is disposed on another side wall of the reagent storage box opposite to the reagent tube; when the rubber film is pressed, the respective one of the reagents in the reagent chamber flows out of the reagent tube and a reagent droplet is formed at an outlet of the reagent tube.

6. The chemiluminescence immunoassay analyzer according to claim 5, wherein a capillary tube storage chamber is formed through partition plates in the capillary tube storage box; the capillary tube storage chamber is wider than a diameter of the capillary tube by 0.5-1 mm, and the capillary tubes are vertically stacked in order inside the capillary tube storage chamber; a first-side through-hole and a second-side through-hole are respectively disposed on a at two opposite sides of a bottom of the capillary tube storage box; the first-side through-hole and the second-side through-hole are both in communication with the capillary tube storage chamber; rubber film flaps capable of being opened or closed are disposed at the first-side through-hole and the second-side through-hole; buffering pads are disposed on side surfaces of the capillary tube storage box and the reagent storage box, circular holes are provided in the buffering pads, and positions of the circular holes are corresponding to positions of the first-side through-hole and the rubber film flaps.

7. The chemiluminescence immunoassay analyzer according to claim 6, wherein, and the positioning assembly is located in front of the pushing assembly; the positioning assembly and the pushing assembly are respectively connected to push-out driving devices, and the push-out driving devices are configured for driving the positioning assembly and the pushing assembly to move on the positioning bracket separately; the press rod is used for pressing the rubber film on the reagent storage box of the storage device in the chemiluminescence immunoassay analyzer; the positioning assembly is used for positioning the first-side through-hole in the capillary tube storage box of the storage device in the chemiluminescence immunoassay analyzer; the pushing assembly is used for pushing the capillary tube out of the second-side through-hole in the capillary tube storage box of the storage device in the chemiluminescence immunoassay analyzer.

8. The chemiluminescence immunoassay analyzer according to claim 7, wherein the positioning assembly comprises a positioning rack, a positioning rod, a blocking plate, and a spring; the positioning rack is connected to one of the push-out driving devices, and the push-out driving device is used for driving the positioning rack to move; the positioning rod is hollow inside, one end of two ends of the positioning rod is tapered and the other end of two ends of the positioning rod is provided with a first limiting boss, and the end of the positioning rod which is tapered is provided with a second limiting boss; the positioning rod is slidably installed on the positioning rack and has the two ends extending out of the positioning rack; the spring and the blocking plate are both sleeved on the positioning rod, the blocking plate is close to the first limiting boss, and the spring is close to the second limiting boss; under an action of the spring, the first limiting boss presses the blocking plate on a side surface of the positioning rack; a push rod in the pushing assembly is configured for passing through the positioning rod to push the capillary tube; the press rod is installed on the positioning rack, and the press rod is shorter than the positioning rod extending from an end of the positioning rack;

the pushing assembly comprises a push rack and the push rod; the push rack is connected to another one of the push-out driving devices, and the another one push-out driving device is configured for driving the push rack to move; one end of the push rod is connected to the push rack and the other end of the push rod extends into the positioning rod and then out of the positioning rod;

the pushing assembly further comprises an adjustment bolt, a threaded hole and a guide hole which are provided in the push rack, the threaded hole is in communication with the guide hole, and the adjustment bolt matches with the threaded hole; the push rod is connected to the push rack through the adjustment bolt; the end of the push rod passes through the guide hole and is fixedly connected to an end of the adjustment bolt and the other end of the push rod extends into the positioning rod; after the positioning rack moves, the push rod extends out of the positioning rod.

9. The chemiluminescence immunoassay analyzer according to claim 8, wherein the positioning assembly further comprises a droplet sensor; the droplet sensor is connected to the push-out driving device in connection with the positioning assembly, and is used for detecting a size of the reagent droplet formed at the outlet of the reagent tube connected to the reagent storage box of the storage device in the chemiluminescence immunoassay analyzer.

10. The chemiluminescence immunoassay analyzer according to claim 1, wherein the waste liquid recycling device is a liquid collection bracket; the liquid collection bracket comprises a horizontal portion and a vertical portion; the vertical portion is perpendicularly connected at a center of the horizontal portion; the horizontal portion is provided with a first groove which is V-shaped, the vertical portion is provided with a guide groove, and the first groove is in communication with the guide groove; the horizontal portion of the liquid collection bracket is located below an outlet of a reagent tube connected to a reagent storage box of the storage device in the chemiluminescence immunoassay analyzer, so that a respective one of the reagents drips from the outlet of the reagent tube into the first groove; the vertical portion of the liquid collection bracket is installed on the bottom plate of the chemiluminescence immunoassay analyzer, and the guide groove is in communication with a liquid collection box disposed below the bottom plate.

* * * * *